United States Patent [19]

Jessel, Jr. et al.

[11] Plant 4,129

[45] Oct. 18, 1977

[54] CHRYSANTHEMUM PLANT

[75] Inventors: Walter H. Jessel, Jr., Doylestown; William E. Duffett, Akron, both of Ohio

[73] Assignee: Yoder Brothers, Inc., Barberton, Ohio

[21] Appl. No.: 716,438

[22] Filed: Aug. 23, 1976

[51] Int. Cl.[2] ..... A01H 5/00

[52] U.S. Cl. ..... Plt./74

[58] Field of Search ..... Plt./74

*Primary Examiner*—Robert E. Bagwill

*Attorney, Agent, or Firm*—Donald D. Jeffery

[57] ABSTRACT

This novel chrysanthemum relates to a white spoon daisy type having good tolerance of high night temperatures.

3 Drawing Figures

The present invention comprises a new and distinct cultivar of *Chrysanthemum morifolium*, Ramat., hereinafter referred to by the cultivar name Frost (No. 72072013).

Frost is a product of a planned breeding program which had the objective of creating new cultivars for use as a cut spray with spoon inflorescence type, with white inflorescence color, with nine week flowering response, and with good tolerance of temperatures higher than 65° F minimum night temperatures for uniform bud development. Such traits in combination were not present in previously available commercial cultivars.

Frost was originated from a cross made in a controlled breeding program in Barberton, Ohio in 1971. The female, or seed parent, was Yellow Daisy Pot (No. 2168AE01; unpatented; commercially available), a light yellow spoon sport of White Daisy Pot (No. 21680E01; unpatented; commercially available). The male, or pollen patent, of Frost was No. 71401003 (unnamed seedling), a white spoon originated by the present inventors from a self-pollination of Illini Spinwheel (No. 21670E02; U.S. Plant Pat. No. 3,379). The parentage of White Daisy Pot and of Illini Spinwheel is unknown to the present inventors.

Frost was discovered and selected as a flowering plant within the progeny of the stated cross by Walter H. Jessel, Jr. and William E. Duffett on Oct. 26, 1972 in a controlled environment in Barberton, Ohio.

The first act of asexual reproduction of Frost was accomplished when vegetative cuttings were taken from the initial selection in January, 1973 in a controlled environment in Barberton, Ohio by a technician working under formulations established and supervised by Walter H. Jessel, Jr. and William E. Duffett. Horticultural examination of selected units initiated May 1, 1973 has demonstrated that the combination of characteristics herein disclosed for Frost are firmly fixed and are retained through successive generations of asexual reproduction.

Frost has not been observed under all possible environmental conditions. The phenotype may vary significantly with variations in environment such as temperature, light intensity, and daylength. The following observations, measurements, and comparisons describe plants grown in Barberton, Ohio under greenhouse conditions which approximate those generally used in commercial practice, as described in Chart A which appears at the end of the present specification. A light intensity chart of general use is shown in ASHAE Trans., Vol. 64, page 64, and reference is made thereto.

The following traits have been repeatedly observed and are determined to be basic characteristics of Frost which in combination distinguish this chrysanthemum as a new and distinct cultivar:

1. Flat inflorescence form.
2. Spooned daisy inflorescence type.
3. White ray floret color, with no pink discoloration with age or with cool temperature (below 60° F) finishes.
4. Yellow-green (immature) to yellow (mature) disc floret color.
5. Uniform nine week flowering response to photoperiodic short day control.
6. Minimal pollen development.
7. Diameter across face of inflorescence from 80 to 95 mm. at maturity.
8. Semi-spreading branching pattern.
9. Medium plant height (requires 1–2 long day weeks prior to short days to produce 72 to 82 cm. height when grown as a single stem plant from May through October).

The accompanying drawings show typical inflorescence and foliage characteristics of Frost. Sheet 1 is a color photograph of Frost as a flowered plant grown as a cut spray. Sheet 2 is a black and white photograph showing three views of the inflorescence of Frost. Sheet 3 is a black and white photograph showing the foliage of Frost at three stages of growth.

Of the many commercial cultivars known to the present inventors, the most similar existing cultivars in comparison to Frost are Illini Spinwheel, the paternal grandparent of Frost, and Spindles (No. 62156001; unpatented). Reference is made to attached Chart B which compares certain characteristics of Frost with those same characteristics of the above mentioned cultivars. General comparisons are as follow:

In comparison to Illini Spinwheel, Frost has larger diameter across face of inflorescence, less pollen, taller plant height, and less pink discoloration of ray florets with age or with cool (below 60° F) finishes. The inflorescence form, inflorescence type, flowering response period and ray floret color of Frost are similar to those same characteristics of Illini Spinwheel.

In comparison to Spindles, Frost has small diameter across face of inflorescence, shorter plant height, and less pink discoloration of ray florets with age or with cool (below 60° F) finishes. The inflorescence form, inflorescence type, flowering response period and ray floret color of Frost are similar to those same characteristics of Spindles.

In the following description, color references are made to The Munsell Limit Color Cascade, 1972 edition. The color values were determined between 8:00 and 8:30 A.M. on May 5, 1976 under 150 foot-candle light intensity at Barberton, Ohio.

Botanical classification: *Chrysanthemum morifolium,* Ramat., cv Frost.

INFLORESCENCE (See Sheets 1 and 2 of drawings)

Capitulum:
- *Form.*—Flat.
- *Type.*—Spooned daisy.
- *Permanence.*—14 to 18 days as a cut flower under average home conditions.
- *Diameter across face.*—80 to 95 mm.

Corolla of ray florets:
- *Color (abaxial).*—White.
- *Color (adaxial).*—White.

Corolla of disc florets:
- *Color (immature).*—22-8.
- *Color (mature).*—26-6.

Reproductive organs:
- *Gynoecium.—Present both ray and disc florets.*
- *Androecium.*—Present disc florets only; scant pollen.

PLANT

General appearance: Semi-spreading branching; medium height.

Foliage (See Sheets 1 and 3 of drawings):
- *Color (abaxial).*—Approximately 19-15.
- *Color (adaxial).*—Approximately 19-13 to 19-14.

We claim:

1. A new and distinct cultivar of *Chrysanthemum morifolium,* Ramat., known by the cultivar name Frost and particularly characterized as to uniqueness by the combined characteristics of flat inflorescence form; spooned daisy inflorescence type; white ray floret color, with no pink discoloration with age or with cool (below 60° F) temperature finishes; yellow-green (immature) to yellow (mature) disc floret color; uniform nine week flowering response to photoperiodic short day control; minimal pollen development; diameter across face of inflorescence from 80 to 95 mm. at maturity; semi-spreading branching pattern; and medium plant height.

CHART A

AVERAGE GREENHOUSE CHRYSANTHEMUM ENVIRONMENTS USED FOR BARBERTON, OHIO

| SEASON | TEMPERATURES USED Night | Bright Day | Cloudy Day | LIGHTING USED | BLACK CLOTH USED | SUPP $CO_2$ |
|---|---|---|---|---|---|---|
| FALL | 65° F to 56° F | 65° F to 80° F | 60° F to 75° F | 2 to 4 weeks at 3 Hours Per Night of 7–10 f.c. | To Sept. 15 on - 5:30 PM Off - 7:30 AM | From Oct. 15 300 ppm |
| WINTER | 58° F to 62° F | 65° F to 70° F | 60° F to 65° F | 2 to 5 weeks at 5 hours Per Night of 7–10 f.c. | NONE | 300 ppm |
| SPRING | 58° F to 65° F | 65° F to 80° F | 60° F to 75° F | 2 to 4 weeks at 5 Hours per Night of 7–10 f.c. | From Mar. 15 on - 5:30 PM Off - 7:30 AM | To Apr. 15 300 ppm |
| SUMMER | 62° F to 68° F | 70° F to 90° F | 65° F to 75° F | 1 to 2 weeks at 3 Hours Per Night of 7–10 f.c. | on - 6:00 PM Off - 8:00 AM | NONE |

CHART B

COMPARISON OF FROST, ILLINI SPINWHEEL AND SPINDLES

| CULTIVAR | INFLORESCENCE FORM AND TYPE | DIAMETER ACROSS FACE OF INFLORESCENCE | OCCURRENCE OF POLLEN | PLANT HEIGHT | FLOWERING RESPONSE PERIOD | RAY FLORET COLOR |
|---|---|---|---|---|---|---|
| Frost | Flat Spooned Daisy | 80 to 95 mm. | Minimal | Medium | 9 week | White |
| Illini Spinwheel | Flat Spooned Daisy | 45 to 60 mm. | Abundant | Short | 9 week | White, tinging pink |
| Spindles | Flat Spooned Daisy | 80 to 100 mm. | Abundant | Tall | 9 week | White, tinging pink |

COMPARISONS MADE OF PLANTS GROWN IN BARBERTON, OHIO UNDER GREENHOUSE CONDITIONS DESCRIBED IN CHART A.

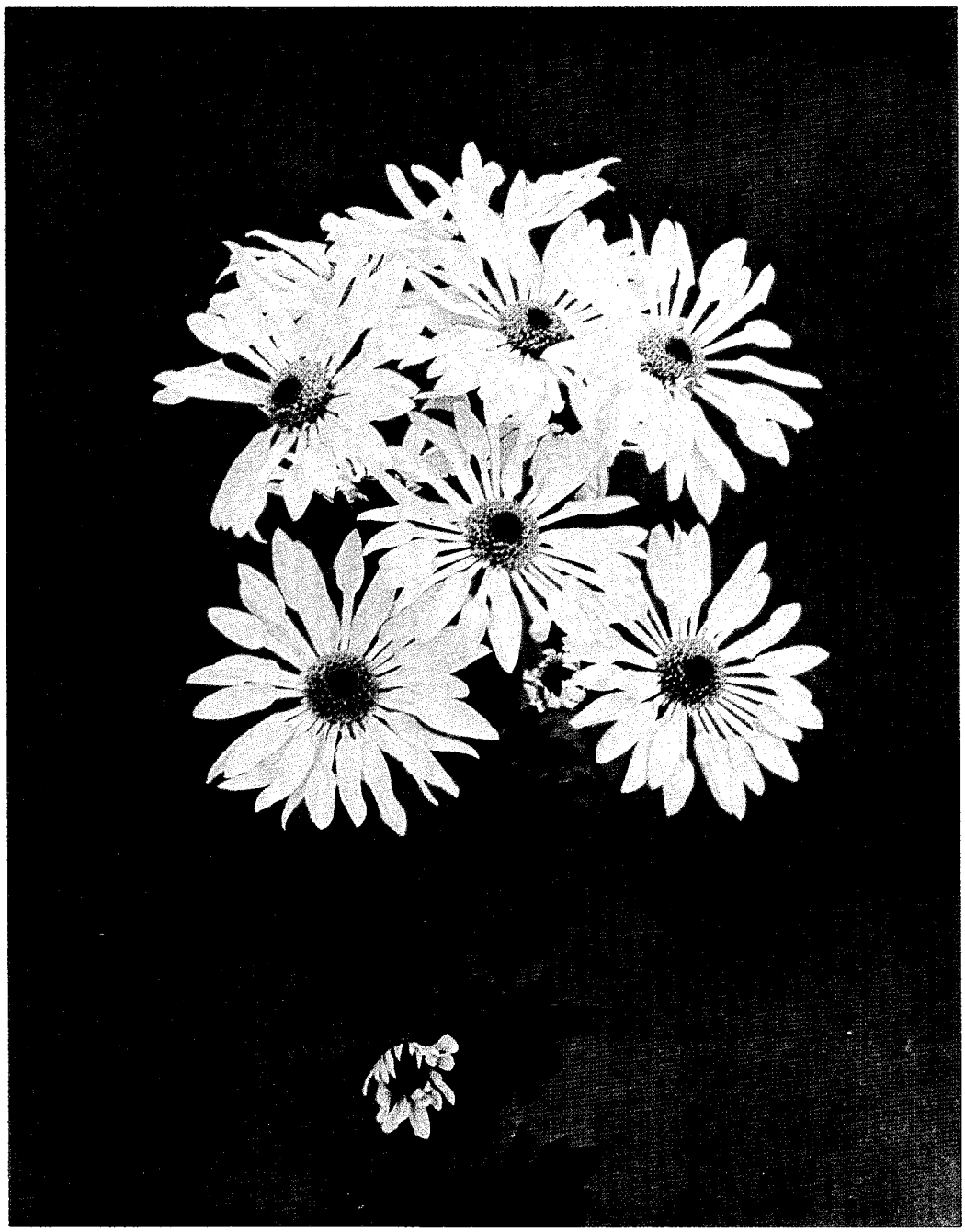

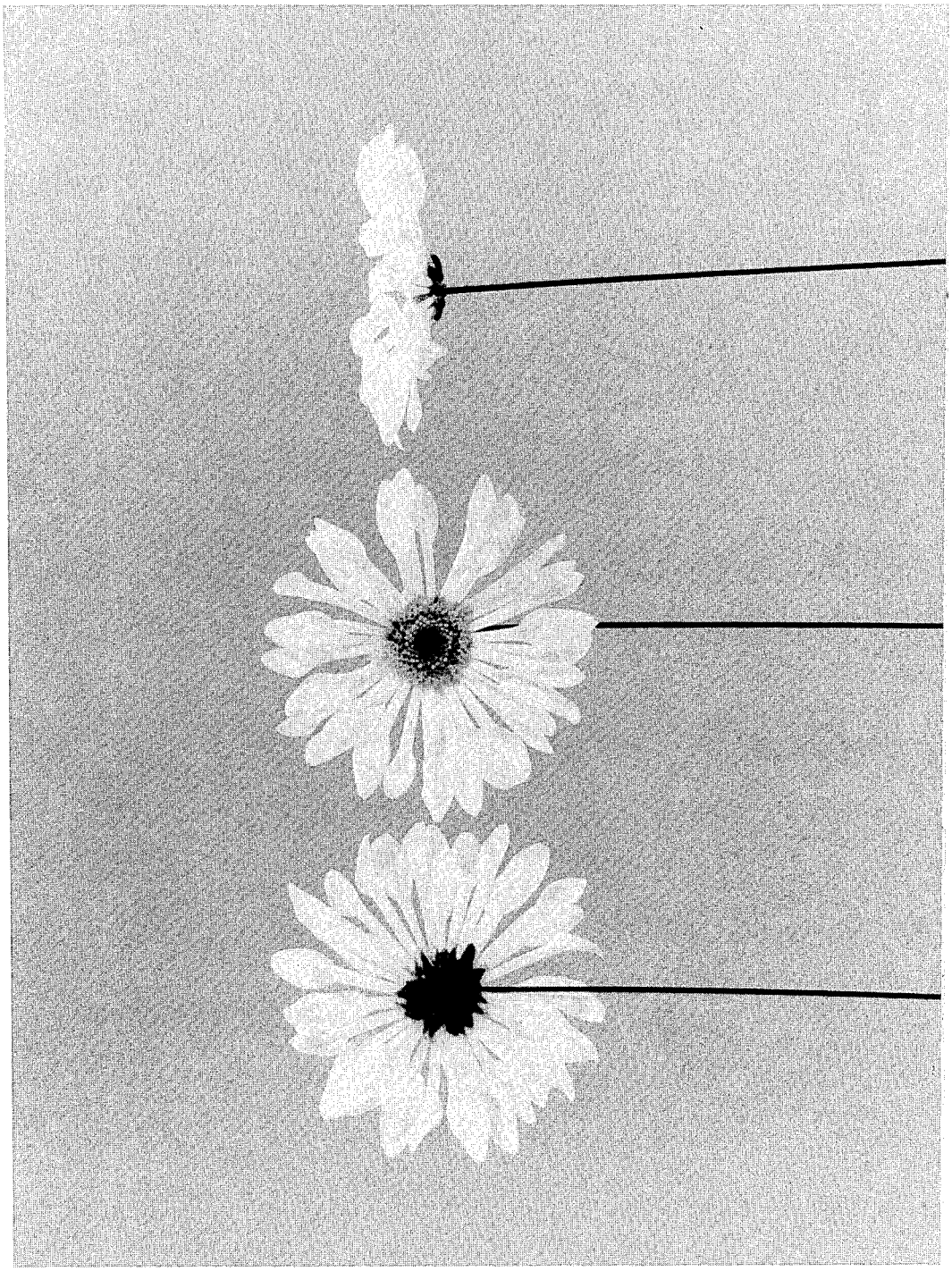

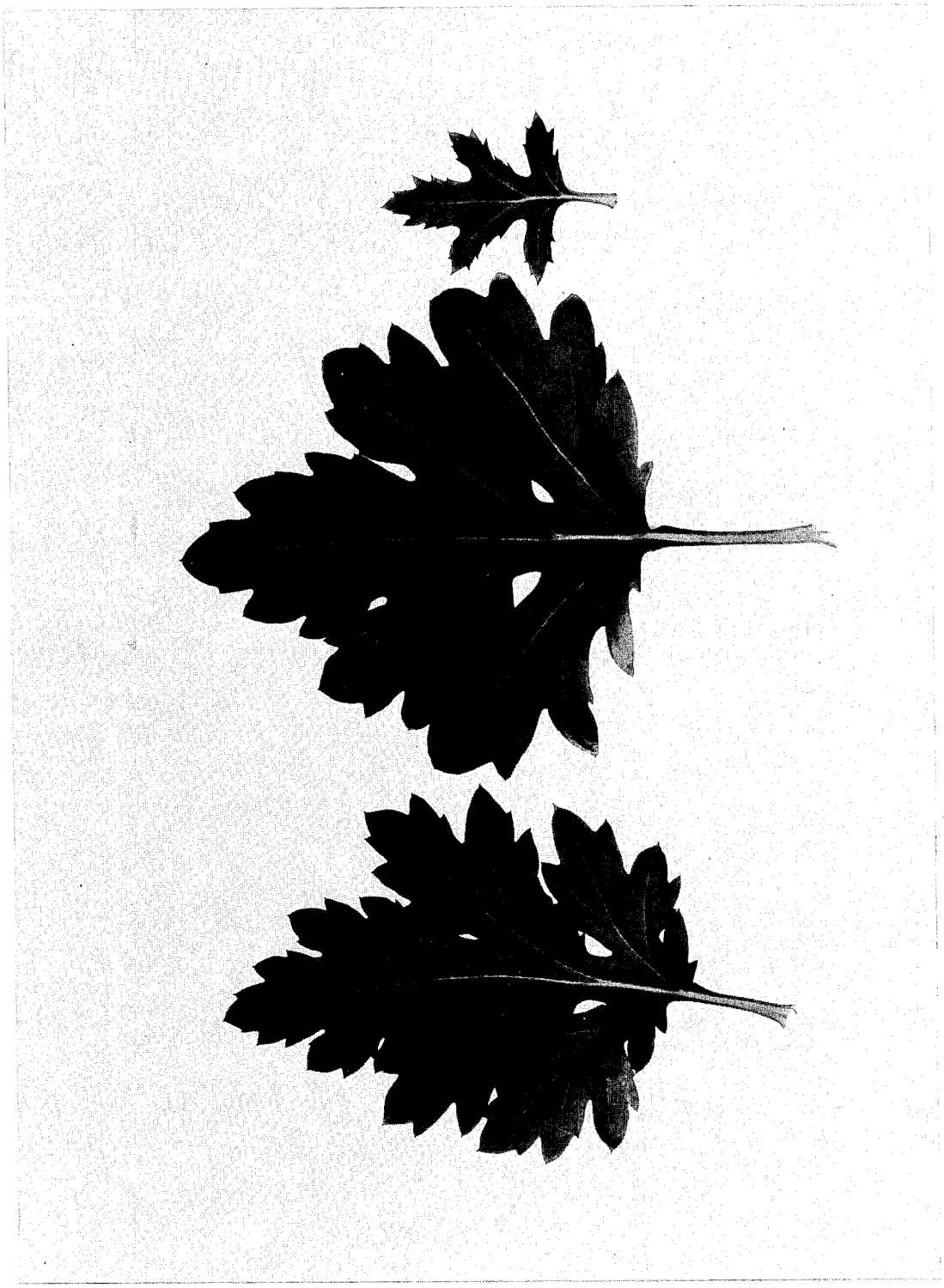

* * * * *